(12) United States Patent
Braun

(10) Patent No.: US 10,736,797 B1
(45) Date of Patent: Aug. 11, 2020

(54) GUARD FOR POST-OPERATIVE STERNAL INCISION

(71) Applicant: Dora F. Braun, Durham, CT (US)

(72) Inventor: Dora F. Braun, Durham, CT (US)

(*) Notice: Subject to any disclaimer, the term of this patent is extended or adjusted under 35 U.S.C. 154(b) by 394 days.

(21) Appl. No.: 15/623,326

(22) Filed: Jun. 14, 2017

Related U.S. Application Data

(60) Provisional application No. 62/350,706, filed on Jun. 15, 2016.

(51) Int. Cl.
| | | |
|---|---|---|
| *A61F 15/00* | (2006.01) | |
| *A41D 13/12* | (2006.01) | |
| *A41D 7/00* | (2006.01) | |
| *A41D 15/00* | (2006.01) | |
| *A41D 13/05* | (2006.01) | |

(52) U.S. Cl.
CPC ............. *A61F 15/008* (2013.01); *A41D 7/00* (2013.01); *A41D 13/0518* (2013.01); *A41D 13/1245* (2013.01); *A41D 15/002* (2013.01)

(58) Field of Classification Search
CPC .. A41D 13/04; A41D 13/046; A41D 13/0518; A41D 13/12; A41D 13/1236; A41D 13/1245; A41D 15/002; A41B 13/10; A61D 9/00; A61F 15/004; A61F 15/008; A61F 13/14; A61F 13/143; A61F 13/148

USPC ........... 602/60–61; 128/888; 2/463, 48, 49.1
See application file for complete search history.

(56) References Cited

U.S. PATENT DOCUMENTS

| | | | | |
|---|---|---|---|---|
| 5,398,343 | A * | 3/1995 | Kuracina | A41D 15/002 2/106 |
| 6,374,415 | B1 * | 4/2002 | Lenart | A41D 13/1236 2/114 |
| 6,450,982 | B1 * | 9/2002 | Peterson | A61F 13/041 24/129 B |
| 6,454,735 | B1 * | 9/2002 | Hamada | A01K 13/006 119/850 |
| 7,004,922 | B1 * | 2/2006 | Shesol | A01K 13/006 119/856 |
| 7,905,553 | B2 * | 3/2011 | Lichtner | A47D 15/006 24/298 |
| 2012/0144547 | A1 * | 6/2012 | Collins | A41D 13/1236 2/67 |
| 2016/0113332 | A1 * | 4/2016 | Wilkes | A41B 13/10 2/49.5 |

\* cited by examiner

*Primary Examiner* — Keri J Nelson
(74) *Attorney, Agent, or Firm* — Ira S. Dorman

(57) ABSTRACT

A guard, fabricated from a water-resistant, lightweight, nonwoven, antimicrobial fabric, is constructed to be worn by a user for protecting a closed, post-operative sternal incision against exposure to water during bathing and showering. The guard avoids the need for manually holding a protective cover over the incision, and thereby frees the arms and hands of the user, or of a caregiver, for washing, lathering and rinsing.

5 Claims, 8 Drawing Sheets

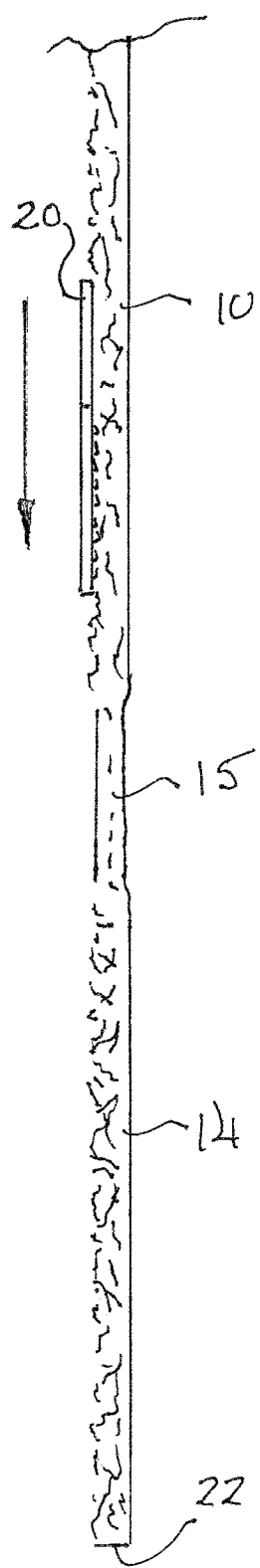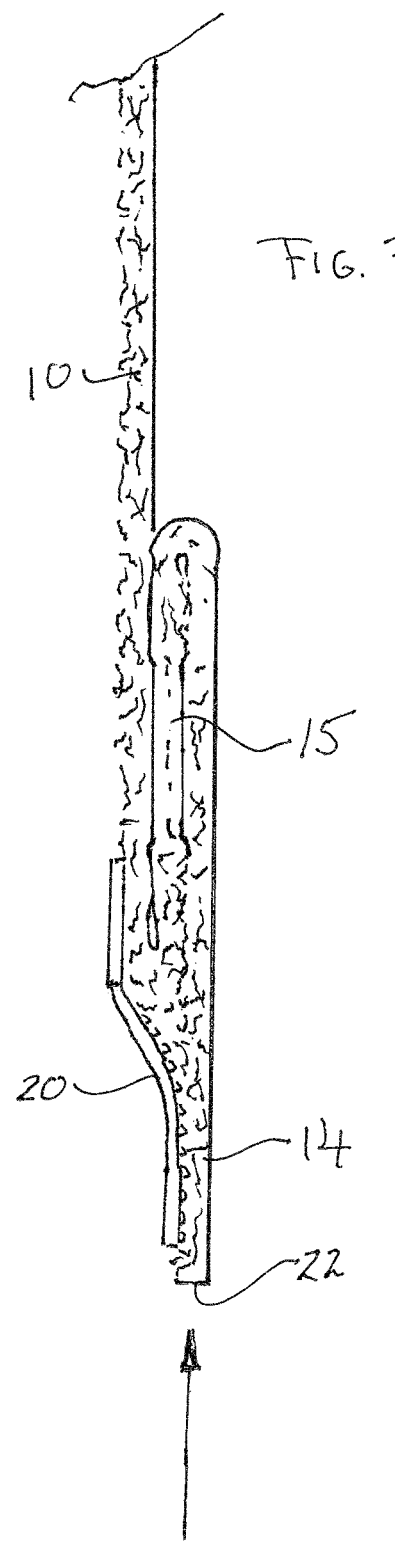

GUARD FOR POST-OPERATIVE STERNAL INCISION

BACKGROUND OF THE INVENTION

The purpose of the guard of the present invention is to help protect a closed, post-operative sternal incision during showering and bathing. It is important to keep such an incision dry, during the healing process, to decrease the risks of irritation and infection; a bandage or dressing, as well as the adhesive properties of any kind of tissue, glue, or adhesive strip applied to the incision, should also be protected against water contact.

It would be highly desirable for a person showering or bathing, post-operatively, to have his or her hands and arms free for body- and hair-washing, lathering, and rinsing, without needing to hold some type of protective cover over the closed incision, thus affording convenience and promoting a sense of independence. In regard to infants and babies, it would be similarly desirable to provide a caregiver with the ability to use both hands for holding and washing the child, making the bathing process much safer while keeping the closed incision dry, or at least substantially so.

Thus, it is the broad object of the present invention to provide a novel guard for the protection of a post-operative sternal incision against exposure to water during showering or bathing. It is a more specific object of the invention to provide such a guard which can be worn by an individual, thus leaving his or her arms and hands, or those of a caregiver, free for washing, lathering, and rinsing. Additional objects of the invention are to provide a guard having the foregoing features and advantages which also affords protection against microorganism growth, is convenient to use, is disposable, recyclable, environmentally conscientious, and inexpensive to manufacture.

BRIEF SUMMARY OF THE INVENTION

It has now been found that the foregoing and related objects of the invention are attained by the provision of a sternal incision guard comprising: a front panel fabricated from a water-repellant, antimicrobial fabric that is normally lightweight and nonwoven; a neck band attached to an upper end portion of the front panel for affixing the guard about the neck of a user; and a waist band attached to a lower end portion of the front panel for affixing the guard about the waist of a user. The front panel has a full length of about 5 to 18 inches and a width of about 0.3 to 10 inches (proportioned appropriately, given the intended use), and has opposite lateral portions that extend between the upper and lower end portions thereof. Resiliently expandable elements, desirably comprising elastic threads or stitching, are incorporated into the front panel along both of its lateral, portions and apply tension to produce shirring and to cause the front panel to have an extended length, along the lateral portions, that is about 50 to 90 percent of the fall length of the fabric thereat.

Normally, both the neck band and the waist band will be of variable effective length, and the guard will include means for disengageably affixing portions of each band in a range of positions for maintaining selected effective lengths of the bands. At full length, the neck band will normally circumscribe an opening of about 10 to 26½ inches and the waistband will normally be about 14 to 44 inches long and about 2½ to 4½ inches wide.

Most desirably, the guard will be fabricated from a fabric having a nappy surface, or fibrous character, on one side, which side will usually be common to the front panel, the neck band, and the waist band; and the means for disengageably affixing will additionally comprise only the hook element, in the form of a tab, of a hook-and-loop type fastener (Velcro) pair. The nappy surface of the one side of the fabric will enable disengageable gripping by the hook-element tab, effectively becoming entangled therein or otherwise secured or held thereby. In any event, at least one side of the fabric used for constructing the guard will be coated or otherwise manufactured to render it smooth, generally glossy, and sufficiently nonporous for the purpose described herein.

The waist band and the front panel of the guard will preferably be constructed to enable variation of the spacing of the bottom margin of the waist band away from the neck band so as to vary the effective length of the guard. This may be achieved by so constructing upper portions of the waist band and lower end portions of the front panel so as to enable parts of those portions to fold inwardly, to lie under an adjacent portion of the front panel, to thereby decrease the spacing of the bottom margin of the waist band away from the neck band. In such embodiments, means will normally be provided for disengageably affixing the a lower end portion of the front panel to the waist band in selected positions across the width of the waist band.

BRIEF DESCRIPTION OF THE SEVERAL VIEWS OF THE DRAWINGS

FIGS. 3A and 3B are schematic views, taken along a longitudinal axis through the guard of the foregoing figures, showing the front panel and waist band thereof unfolded and with a suitably positioned fastening tab attached and affixed to the front panel (3A), and showing the panel and waist band folded with portions of the waist band and the pulled down front panel disposed inwardly (3B) and secured with the fastening tab affixed to the waist band.

DETAILED DESCRIPTION OF THE PREFERRED AND ILLUSTRATED EMBODIMENTS

Turning now in detail to FIGS. 1, 2, 3A and 3B of the drawings, therein illustrated is a guard, for protection of a post-operative sternal incision, embodying the invention. The guard is comprised of a front panel or bodice 10, functioning as a chest- or anterior torso covering portion, a neck band comprised of curved arms 12 that are integrally formed and merge with the front panel 10 at its upper end and that are symmetrical about its centerline, and a waist band or belt 14 that extends transversely of the centerline and laterally beyond bottom of the panel. As indicated by shading, the surface of the fabric providing the front of the guard is nappy and the surface providing the back is smooth and glossy.

Figure 1:
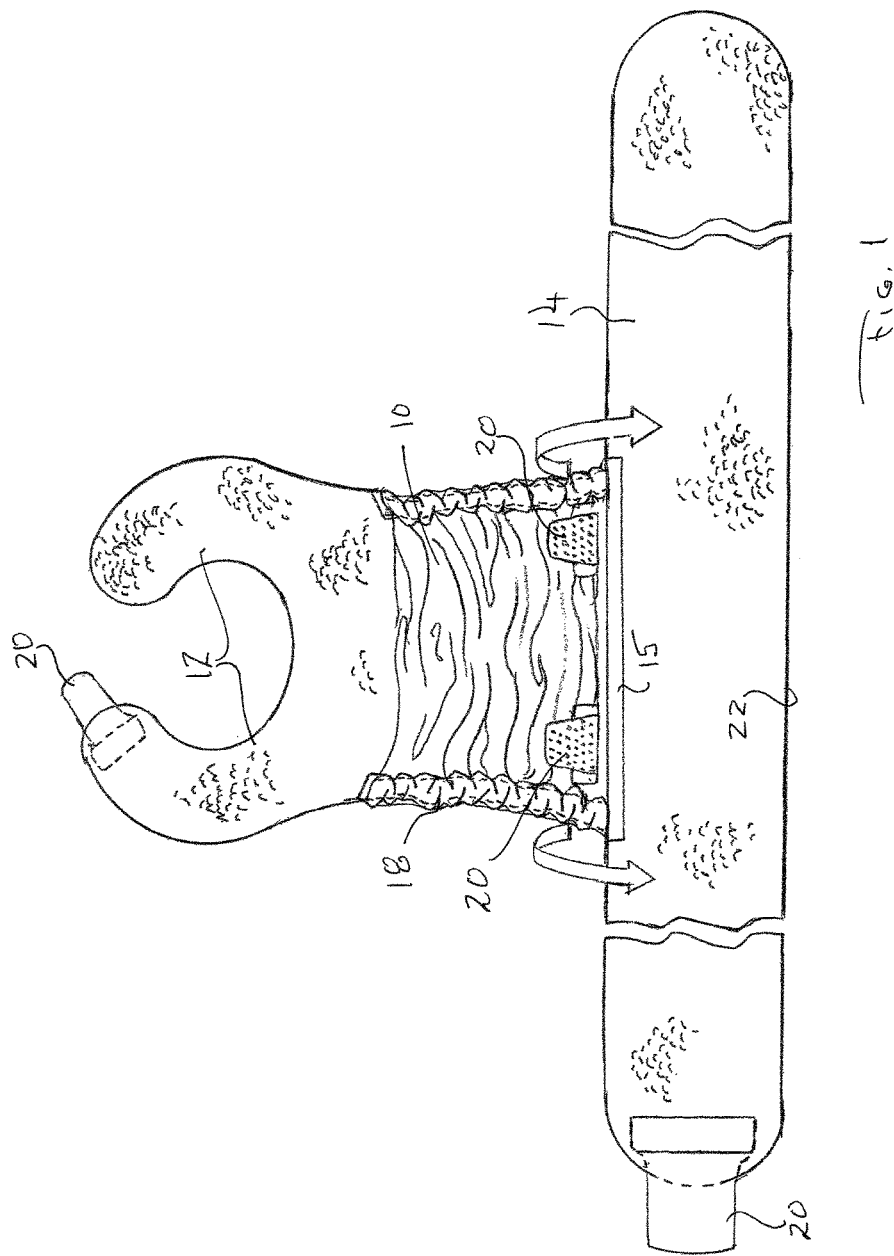
FIG. 1 is a front plan view of a guard, for protection of a post-operative sternal incision, embodying the present invention.
Figure 2:
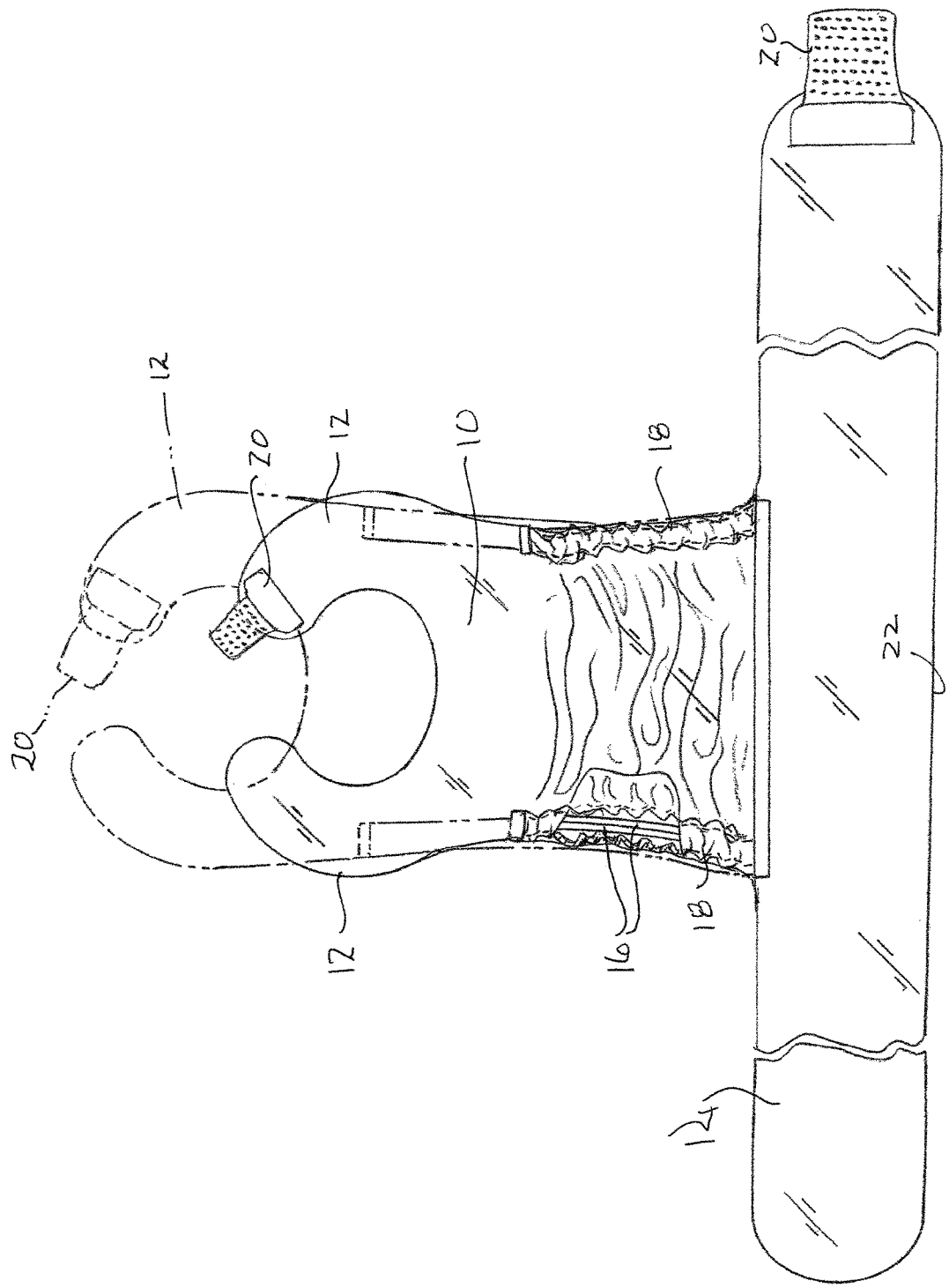
FIG. 2 is a back plan view of the guard of FIG. 1.

Elastic threads 16 (visible in the broken-away section of the front panel 10 in FIG. 2) extend through and along the opposite lateral margins and produce, in their relaxed state, shirring or shirred sections 18 thereat and bunching of the panel 10, as illustrated in FIG. 1 and FIG. 2 (full-line representation). Tension applied longitudinally between the neck band and the waist band 12,14 extends the threads 16 and increases the effective length of the panel 10, bringing the neck band 12 to an extended relationship, such as is represented by the phantom-line depiction in FIG. 2.

Figure 4:
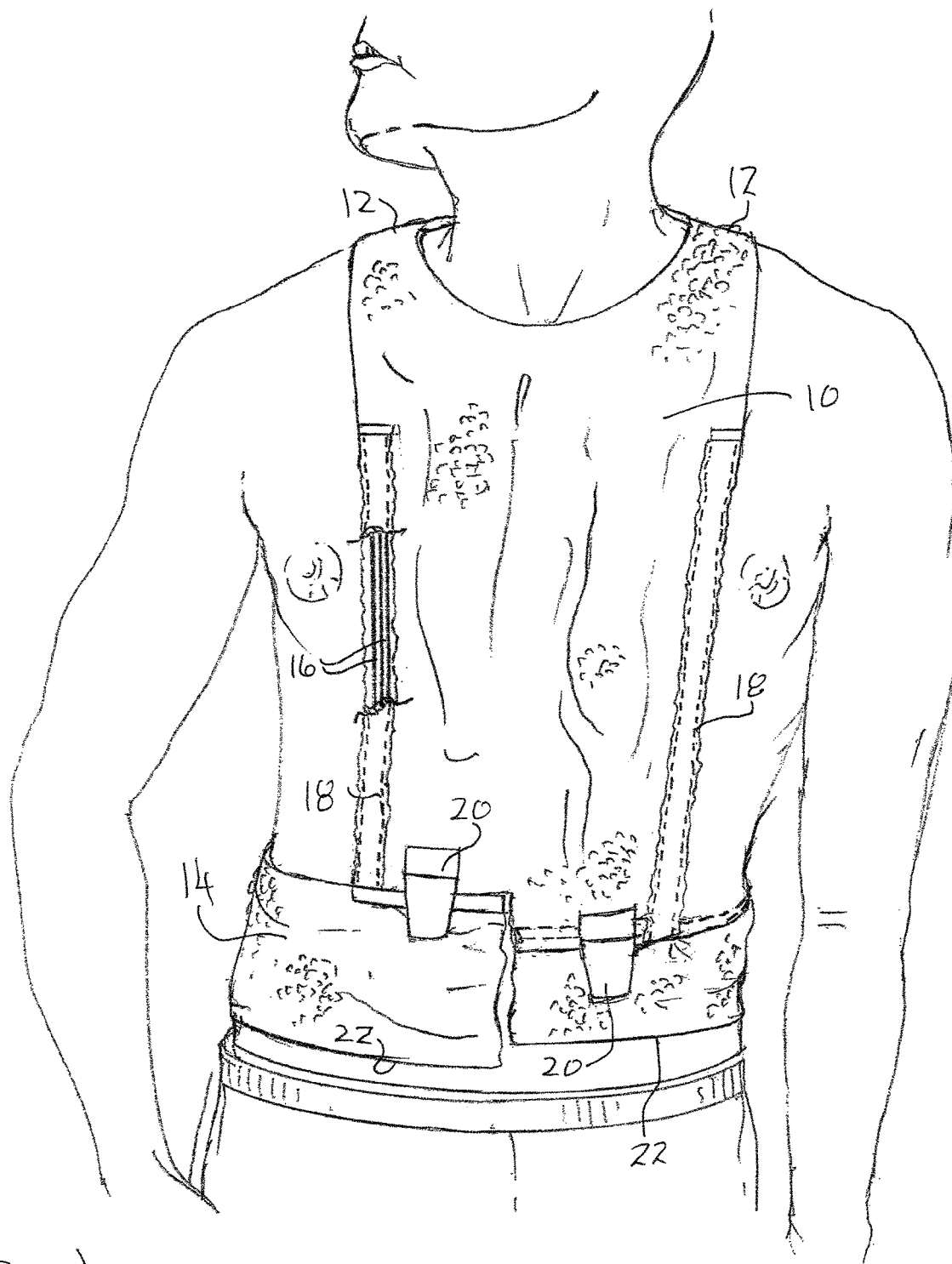
FIG. 4 is a front perspective view of the guard of the foregoing figures worn by an adult male patient, with portions of the guard broken away and showing, to the left of center, an unfolded arrangement and, to the right of center, an arrangement in which the bottom margin of the waist band has been elevated by folding and inward disposition of the fabric, it being appreciated that two arrangements are shown for convenience of illustration and that it is not intended that both arrangements be taken as being optimally fit to the wearer's body.
Figure 5:
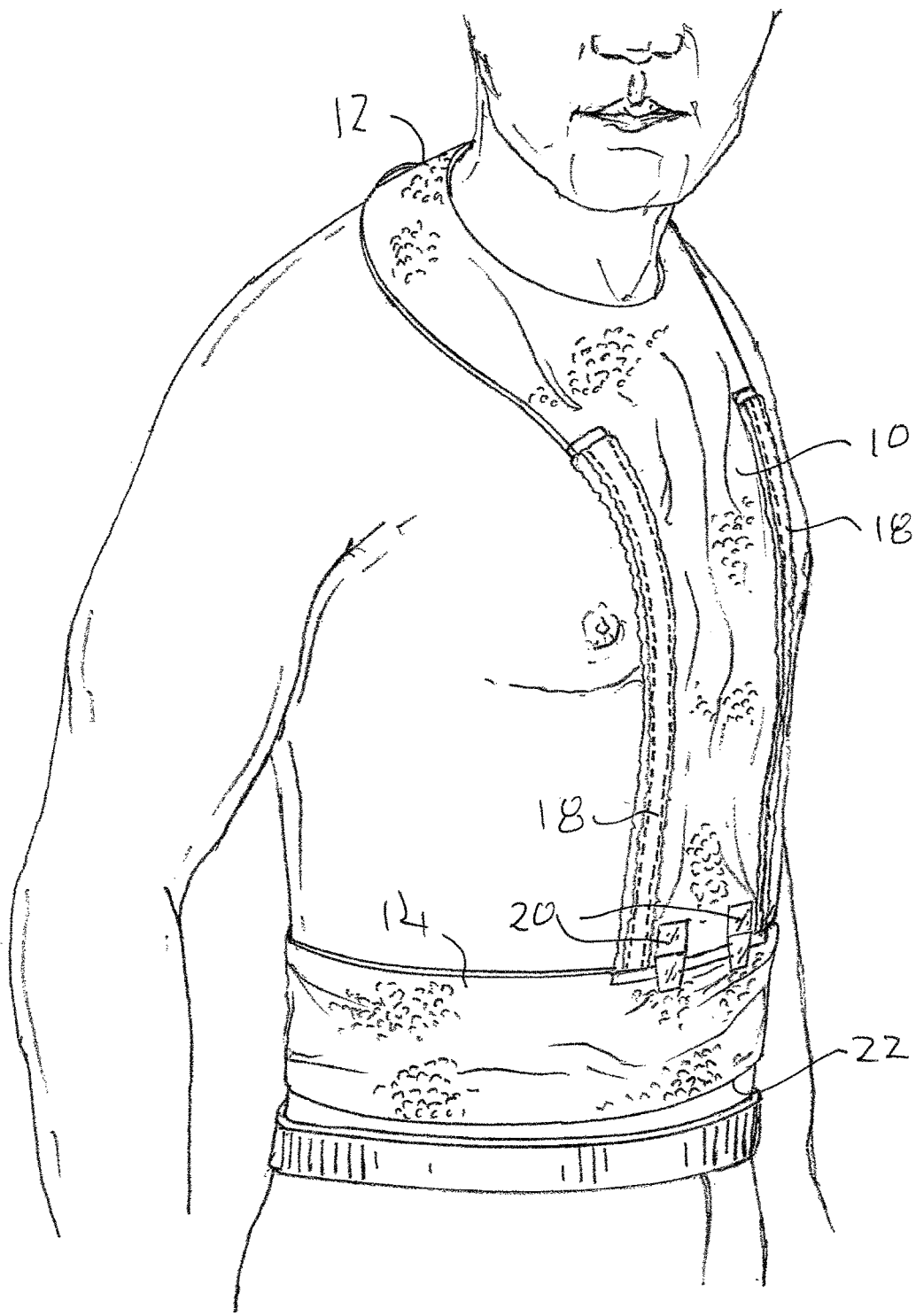
FIG. 5 is a perspective view, taken from an oblique angle to the right of the guard-wearing patient of FIG. 4 (left of center arrangement only).
Figure 6:
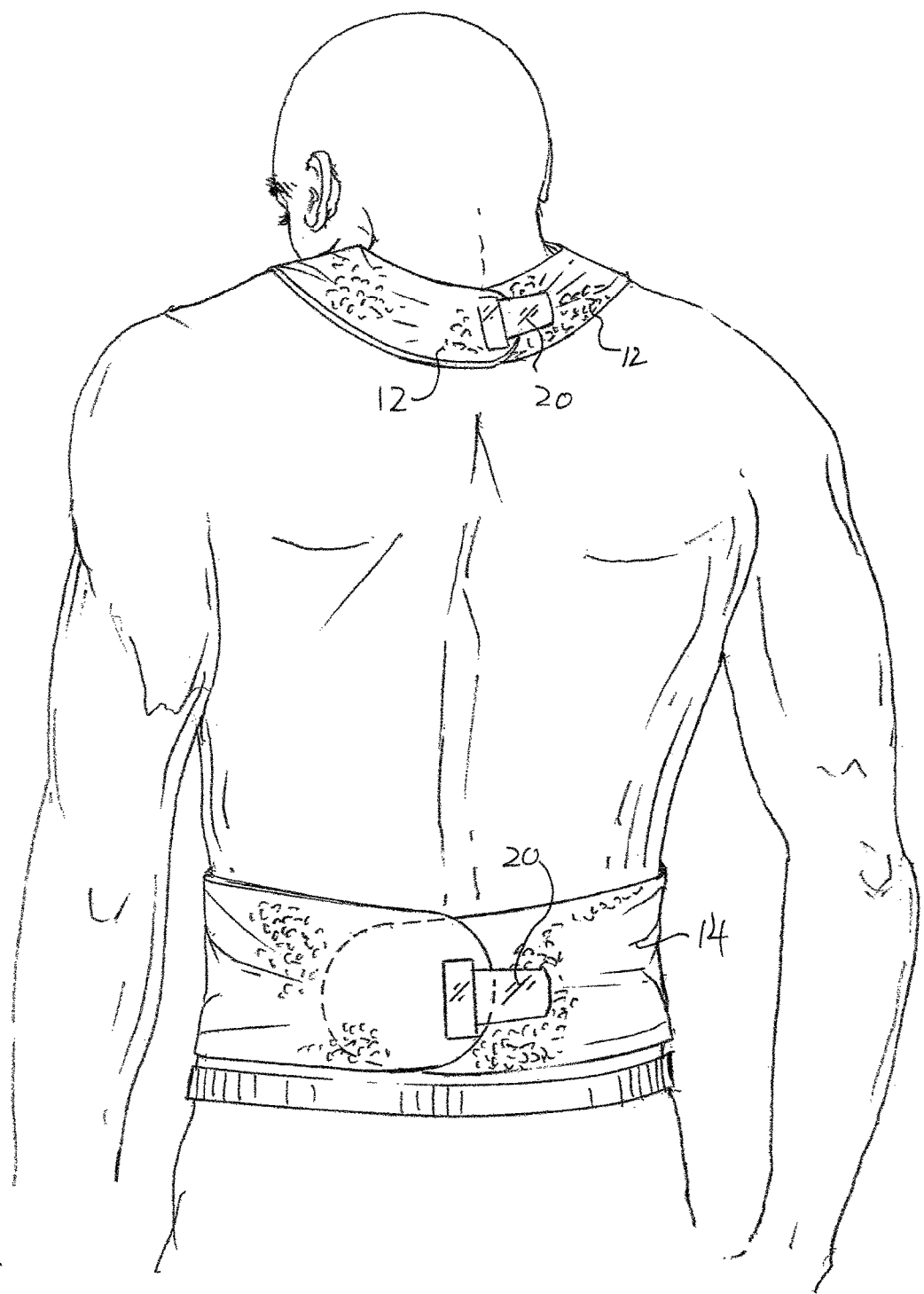
FIG. 6 is a back view of the guard-wearing patient of FIGS. 4 and 5.

As a result, and as seen in FIGS. 4 and 5, when the neck band 12 and the waist band 14 are optimally adjusted and the guard is otherwise properly fitted (as by folding of the front panel and waist band portions, if necessary and as described herein), the panel 10 will be brought into close conformity to the wearer's anterior torso, with the lateral margins closely and dynamically following his body contours and substantially avoiding gaps therealong, thereby minimizing the ingress of water to the site of the sternal incision. In addition, moreover, tension generated along its lateral margins will normally cause the panel 10 to assume a somewhat concave or bunched configuration, spacing it away from the wound and its covering or dressing and thereby minimizing irritation and potential contamination.

As is also seen in FIGS. 1, 2, and 3, one element of a hook-and-loop type fastener (Velcro) pair, in, the form of a tab 20 bearing schematically indicated functional "hooks" on one face, is attached near the free end of one of the neck band arms 12 and near one of the ends of the waist band 14. In this preferred embodiment the fabric used for fabrication of the guard should not only exhibit water-resistant and antimicrobial properties, but it will also have (as indicated above) one surface (most desirably the outermost surface) with a nappy or fibrous character, the other surface being plain, smooth, flat, and perhaps glossy, to impart the desired water-resistance.

The nappy surface of the fabric will provide effective "loops" or other gripping feature on the outer surface of the guard of the illustrated embodiment, to enmesh, grip, or otherwise engage the "hooks" of the fastening tabs 20 when pressed thereagainst. This construction of course enables the tabs 20 to engage the fabric at any location on its nappy surface, thereby affording virtually unlimited variation of the points of interengagement to one another of the neck band arms 12 and the free opposite end portions of the waist band 14. Suitable fabrics for fabrication of such a guard are commercially available from a number of sources, including Novo Enterprise Company, of California, under the trade designation NOVOPET, and from WPT Nonwovens Corporation, of Kentucky, under the trade designation WPT NONWOVENS.

As seen in FIGS. 3B and 4, an upper portion of the waist band 14 and a lower end portion of the front panel 10, attached to one another in the transversely extending narrow area 15, may be folded and partially disposed behind an adjacent portion of the panel 10, extending the panel 10 lengthwise to do so and reducing its effective length and the effective width of the band 14, thereby effectively shortening the guard (as indicated by the upwardly directed arrow in FIG. 3B), As can also be seen, a "hook"-bearing fastening tab 20 is attached to the outside surface of a the lower portion of the front panel 10 (as shown in FIG. 1, two such tabs 20 are provided side-by-side and to opposite sides of a centerline) to maintain the folded fabric parts in selected position. Thus, if the guard is too long when the neck band 12 and the waist band 14 are secured on the user, an optimal fit can be achieved simply by grasping the two side-by-side tabs 20 and using them to pull the lower end portion of the panel 10 over an upper portion of the waist band 14 (as indicated by the open arrows in FIG. 1, and the downwardly directed arrow in FIG. 3A), and then pressing the tabs 20 against the nappy surface of the waist band to secure the arrangement. It should be appreciated that disposing the folded parts inwardly, to lie against the inside surface of the adjacent panel portion, prevents creation of a trough-like formation to in turn prevent the accumulation, or pooling, of water.

Figure 7:
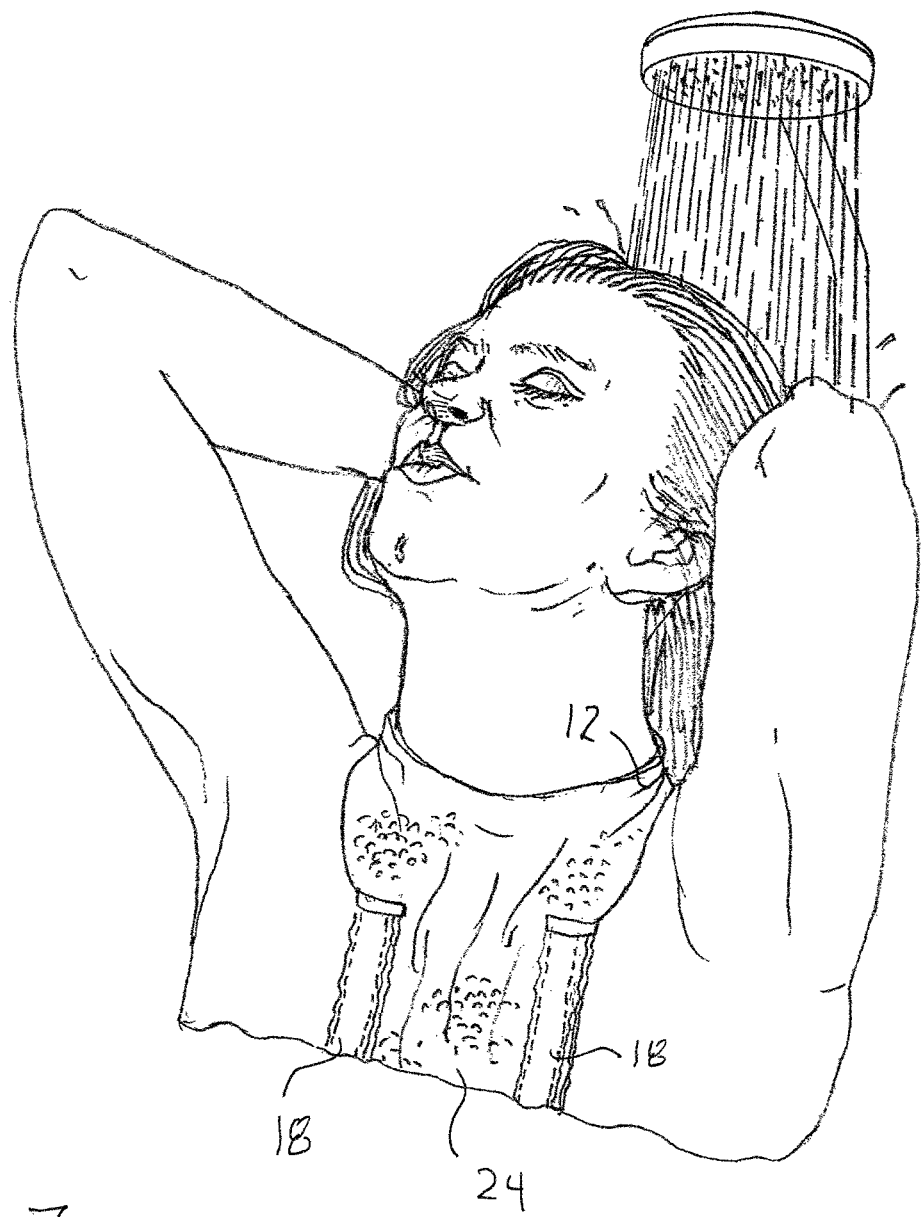
FIG. 7 is a front perspective view of an adult female patient wearing a differently proportioned sternal incision guard embodying the present invention, fragmentarily illustrated.

Turning now in detail to FIG. 7, the guard illustrated therein is worn by a female adult and varies from the guard depicted in the foregoing figures essentially by virtue of the relative narrowness of the front panel 24 of which it is comprised. The figure illustrates the freedom of arm and hand movement that is enabled by the avoidance of any need for manually holding an object over an incision, to keep it dry.

Figure 8:
FIG. 8 is a front perspective view of an infant wearing a sternal incision guard embodying the invention.

Turning finally to FIG. 8 of the drawings, the construction of the guard shown therein is again essentially the same as that of the guards previously illustrated, but it is intended for use on infants and babies and is of course therefore of commensurately smaller dimensions. For example, the front panel 26 would typically be about 3 to 4 inches wide and about 5 to 7 inches long; the inside circumference of the neck band defined by the fastened arms 12 would typically be about 10 to 12 inches; and the waist band 14 would typically be about 14 to 16 inches long.

It will be appreciated that the sternum guards of the invention may be offered in standard sizes, or may be custom fit. For example, standard sizes may be extra small, small, medium, large, extra-large and extra-extra large; a size may be offered specifically for use for infants, babies, and toddlers. It will also be appreciated that the guards of the invention are not gender-specific; by providing them in a range of sizes, and with their elasticized lateral margins, the guards may be used interchangeably by males and females.

Although the preferred fabrics for use in constructing the guards of the invention have been described above, it will be appreciated by those skilled in the art that their characteristics, and the manner of providing them, are subject to considerable variation; the characteristics may be inherent or may be produced by use of coatings, treatments, applied substances, etc. For example, a product bearing the trade designation AGION, available from Sciessent of Wakefield, Mass., may be applied to a fabric to impart desired antimicrobial properties for protection against microorganism viability and growth, as is particularly important at sites of closed incisions.

It will be appreciated that, as used herein, the term "water-resistant" is intended to broadly encompass fabrics including those that may be described as "waterproof," "water-repellant," etc., as long as the fabric provides substantial protection against water penetration (being not inconsistent, however, with some degree of porosity to afford desired "breathability"). The fabric used should be inexpensive, to best accommodate disposability (albeit desirably also readily washable, by hand or machine, and dryable), recyclable, environmentally friendly, and generally of the lightest weight possible so as to afford comfort, avoid interference in use, and facilitate packaging and shipping. Often, nonwoven fabrics, made from recycled cellulosic materials, will best achieve these and other ends. It will be appreciated that it is not necessary that all portions of the guard be made from the same fabric.

While the "hook" element of a hook-and-loop fastener pair is preferably used in cooperation with a nappy-surfaced fabric in practicing the present invention, other means for disengageably affixing portions of the guard to one another may be employed instead. For example, both components of a Velcro fastener pair may provide the affixing means, and snap fasteners, hooks-and-eyes, and other kinds of fasteners may be utilized, as appropriate. And while elastic threads are described as the resiliently expandable elements by which the necessary shirring is produced, bands and other functionally equivalent elements may of course be employed, if so desired.

Thus, it can be seen that the present invention provides a novel guard for the protection of a post-operatative sternal incision against exposure to water during showering or bathing. The guard worn by an individual leaves his or her arms and hands, or those of a caregiver, free for washing, lathering, and rinsing; it provides protection against microorganism growth, is convenient to use, is disposable, recyclable, environmentally conscientious, and is inexpensive to manufacture.

Having thus described the invention, what is claimed is:

1. A sternal incision, guard comprising: a front panel fabricated from a water-repellant, antimicrobial fabric having a full length of about 5 to 18 inches and a width of about 3 to 10 inches, said front panel having an upper end portion, a lower end portion, and generally rectilinear opposite lateral portions extending between said upper and lower end portions, and having resiliently expandable elements incorporated, into said front panel along both of said lateral portions thereof and applying tension thereat to produce shirring therealong and to cause said front panel to have an unextended length, along said lateral portions, that is about 50 to 90 percent of the full length of said fabric thereat; a neck band attached to said upper end portion of said front panel for affixing said guard about the neck of a user; and a waist band attached to said lower end portion of said front panel for affixing said guard about the waist of a user, said waist band being 2½ to 4½ inches wide and extending continuously transversely of a centerline of said front panel and laterally beyond each of said, opposite lateral portions thereof; said front panel including means, on an outermost side thereof, as said guard is intended to be worn, for disengageably affixing said lower end portion of said front panel in multiple selected positions on an outermost side of said waist band, at least said waist band being fabricated from a fabric having a nappy surface on said outermost side thereof; and said means for disengageably affixing comprising two tabs hingedly attached to said lower portion of said front panel on said outermost side of said front panel and positioned side-by-side to opposite sides of said centerline, each of said tabs comprising a hook element of a hook-and-loop type fastener pair and having a free lower end portion bearing, on an underside thereof, the hooks of said hook element, said nappy surface on said outermost side of said waist band being constructed for disengageable enmeshing therewith of said hook elements of said tabs, and said multiple selected positions of disengageable affixing including virtually all positions across the width of said waist band; whereby part of said lower end portion of said front panel may be folded inwardly to lie under an adjacent portion of said front panel and disengageably affixed in such position, using said tabs, to thereby decrease the spacing of a bottom margin of said waist band away from said neck band.

2. The guard of claim 1 wherein said expandable elements incorporated into said font panel comprise elastic threads.

3. The guard of claim 1 wherein both said neck band and said waist band are of variable effective length, and wherein each of said neck band and said waist band includes, on and end portion thereof, a hook element of a hook-and-loop type fastener pair for disengageably affixing portions of said neck band and said waist band at various positions for maintaining selected effective lengths of said neck band and said waist band, said front panel and said neck band being fabricated from a fabric having a nappy surface, on, respectively, said outermost side of said front panel and on an outermost side of said neckband.

4. The guard of claim 1 wherein a reverse side of said fabric, reverse to said outermost side, is of smooth, flat, substantially nonporous character.

5. The guard of claim 4 wherein said fabric is nonwoven.

* * * * *